(12) United States Patent
Pandey

(10) Patent No.: US 10,368,899 B2
(45) Date of Patent: Aug. 6, 2019

(54) SURGICAL TOOL FOR CORING PRECISE HOLES AND PROVIDING FOR RETRIEVAL OF TISSUE

(75) Inventor: Rajesh Pandey, Plantation, FL (US)

(73) Assignee: HeartWare, Inc., Miami Lakes, FL (US)

( * ) Notice: Subject to any disclaimer, the term of this patent is extended or adjusted under 35 U.S.C. 154(b) by 970 days.

(21) Appl. No.: 11/332,016

(22) Filed: Jan. 13, 2006

(65) Prior Publication Data

US 2007/0167968 A1   Jul. 19, 2007

(51) Int. Cl.
*A61B 17/3205* (2006.01)
*A61B 17/11* (2006.01)
*A61B 17/00* (2006.01)

(52) U.S. Cl.
CPC ........ *A61B 17/32053* (2013.01); *A61B 17/11* (2013.01); *A61B 2017/00252* (2013.01); *A61B 2017/1107* (2013.01)

(58) Field of Classification Search
CPC .............. A61B 17/11; A61B 17/32053; A61B 17/3205; A61B 2017/00247; A61B 2017/00252; A61B 2017/1107; A61B 17/32075
USPC .................. 606/184, 185, 167, 170; 600/16; 623/2.38, 2.39, 2.4, 2.41
See application file for complete search history.

(56) References Cited

U.S. PATENT DOCUMENTS

| | | | |
|---|---|---|---|
| 3,776,237 A | 12/1973 | Hill et al. | |
| 4,018,228 A | 4/1977 | Goosen | |
| 4,461,305 A | 7/1984 | Cibley | |
| 5,129,913 A | 7/1992 | Ruppert | |
| 5,139,508 A * | 8/1992 | Kantrowitz | ...... A61B 17/32053 606/172 |
| 5,324,300 A | 6/1994 | Elias et al. | |
| 5,488,958 A | 2/1996 | Topel et al. | |
| 5,653,705 A * | 8/1997 | de la Torre | ........ A61B 17/3423 606/1 |
| 5,690,662 A | 11/1997 | Chiu et al. | |
| 5,695,504 A * | 12/1997 | Gifford et al. | ................. 606/153 |
| 5,827,316 A | 10/1998 | Young et al. | |

(Continued)

FOREIGN PATENT DOCUMENTS

| | | |
|---|---|---|
| EP | 0637435 A1 | 2/1995 |
| WO | WO 02/45602 A | 6/2002 |
| WO | 2007084340 A2 | 7/2007 |

OTHER PUBLICATIONS

International Preliminary Report on Patentability issued by the International Bureau of WIPO in connection with International Application No. PCT/US2007/000764.

(Continued)

*Primary Examiner* — Sarah A Simpson
(74) *Attorney, Agent, or Firm* — Christopher & Weisberg, P.A.

(57) ABSTRACT

A tool for coring a hole in a patient's body. A housing includes a first opening and a second opening and has an axis extending therebetween. A shaft is movably positioned along the axis. A blade assembly is attached to one end of the shaft. The blade assembly comprises a cup having an open end and a closed end and a cutting edge formed around the open end. An interface is attached to the housing, which is shaped and dimensioned to communicate with a connector used to connect a medical device to a the patient's body.

16 Claims, 2 Drawing Sheets

(56) References Cited

U.S. PATENT DOCUMENTS

| | | |
|---|---|---|
| 5,965,504 A | 10/1999 | Reynolds |
| 5,972,014 A * | 10/1999 | Nevins ............. A61B 17/32053 |
| | | 604/165.02 |
| 5,980,545 A | 11/1999 | Pacala et al. |
| 6,033,419 A | 3/2000 | Hamblin, Jr. et al. |
| 6,036,657 A | 3/2000 | Milliman et al. |
| 6,080,173 A | 6/2000 | Williamson, IV et al. |
| 6,080,176 A | 6/2000 | Young |
| 6,117,130 A | 9/2000 | Kung |
| 6,162,214 A | 12/2000 | Mueller et al. |
| 6,171,251 B1 | 1/2001 | Mueller et al. |
| 6,652,552 B2 | 11/2003 | DuMontelle |
| 6,695,859 B1 * | 2/2004 | Golden et al. ................. 606/184 |
| 6,726,648 B2 * | 4/2004 | Kaplon et al. ..................... 604/9 |
| 6,732,501 B2 * | 5/2004 | Yu et al. ......................... 600/16 |
| 6,863,677 B2 * | 3/2005 | Breznock ....................... 606/184 |
| 2001/0020139 A1 | 9/2001 | Milliman et al. |
| 2002/0177865 A1 | 11/2002 | McIntosh |
| 2003/0023255 A1 | 1/2003 | Miles et al. |
| 2003/0040765 A1 * | 2/2003 | Breznock ....................... 606/184 |
| 2004/0049221 A1 | 3/2004 | Loshakove et al. |
| 2004/0073247 A1 * | 4/2004 | Loshakove et al. .......... 606/184 |
| 2004/0236170 A1 * | 11/2004 | Kim ................................. 600/16 |
| 2005/0101983 A1 * | 5/2005 | Loshakove et al. .......... 606/185 |
| 2005/0154411 A1 * | 7/2005 | Breznock et al. ............. 606/184 |
| 2005/0251187 A1 * | 11/2005 | Beane et al. .................. 606/180 |
| 2006/0247498 A1 * | 11/2006 | Bonadio ............ A61B 17/3423 |
| | | 600/208 |
| 2007/0066943 A1 * | 3/2007 | Prasad et al. .................. 604/264 |
| 2007/0134993 A1 * | 6/2007 | Tamez et al. .................. 439/752 |
| 2007/0167968 A1 | 7/2007 | Pandey |
| 2007/0167969 A1 | 7/2007 | Pandey |
| 2009/0012552 A1 | 1/2009 | Pandey et al. |

OTHER PUBLICATIONS

Written Opinion of the International Searching Authority issued by the International Searching Authority (ISA/US) in connection with International Application No. PCT/US2007/000764.

Communication from the Search Division of the European Patent Office dated Nov. 27, 2009 in connection with European Patent Application No. 07709706.1.

Supplementary European Search Report issued by the Search Division of the European Patent Office dated Nov. 18, 2009 in connection with European Patent Application No. 07709706.1.

International Search Report issued by the International Searching Authority (ISA/US) in connection with International Application No. PCT/US07/00764.

Written Opinion of the International Searching Authority issued by the International Searching Authority (ISA/US) in connection with International Application No. PCT/US07/00764.

* cited by examiner

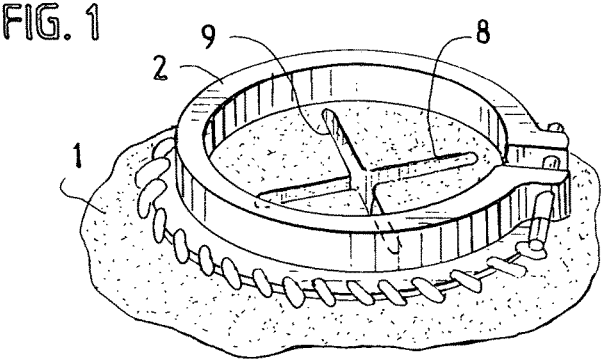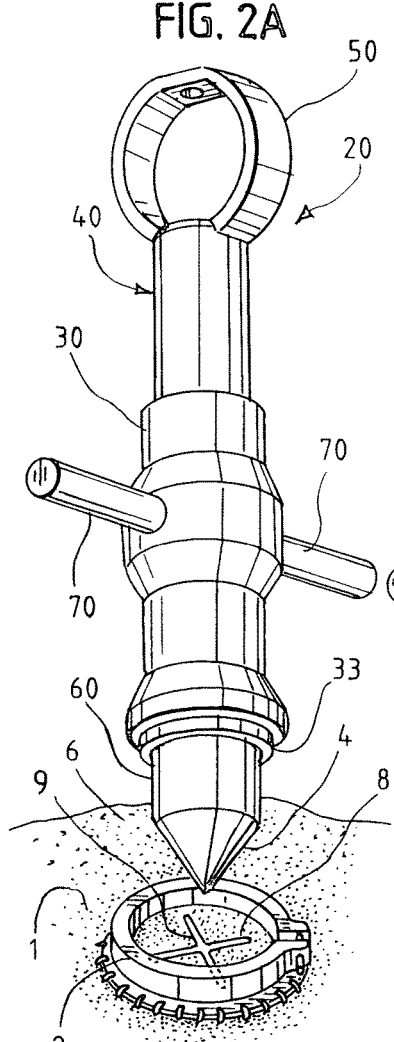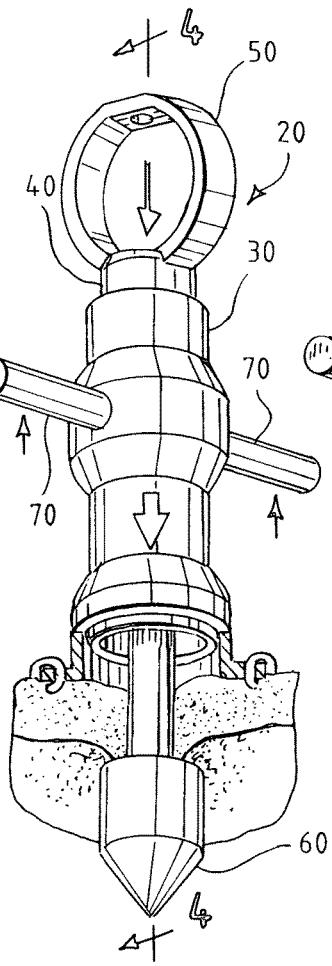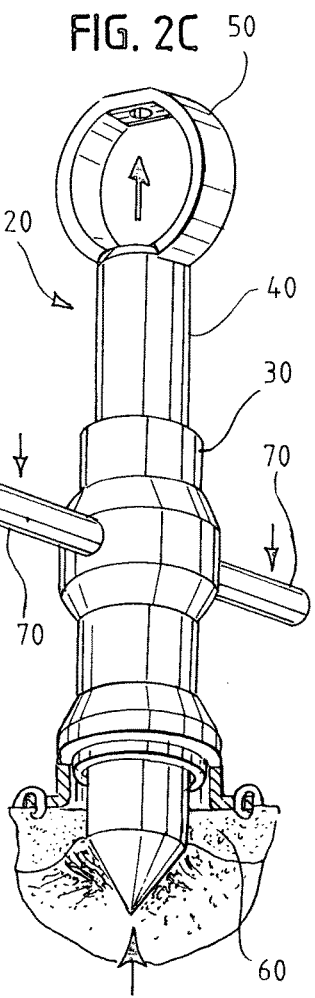

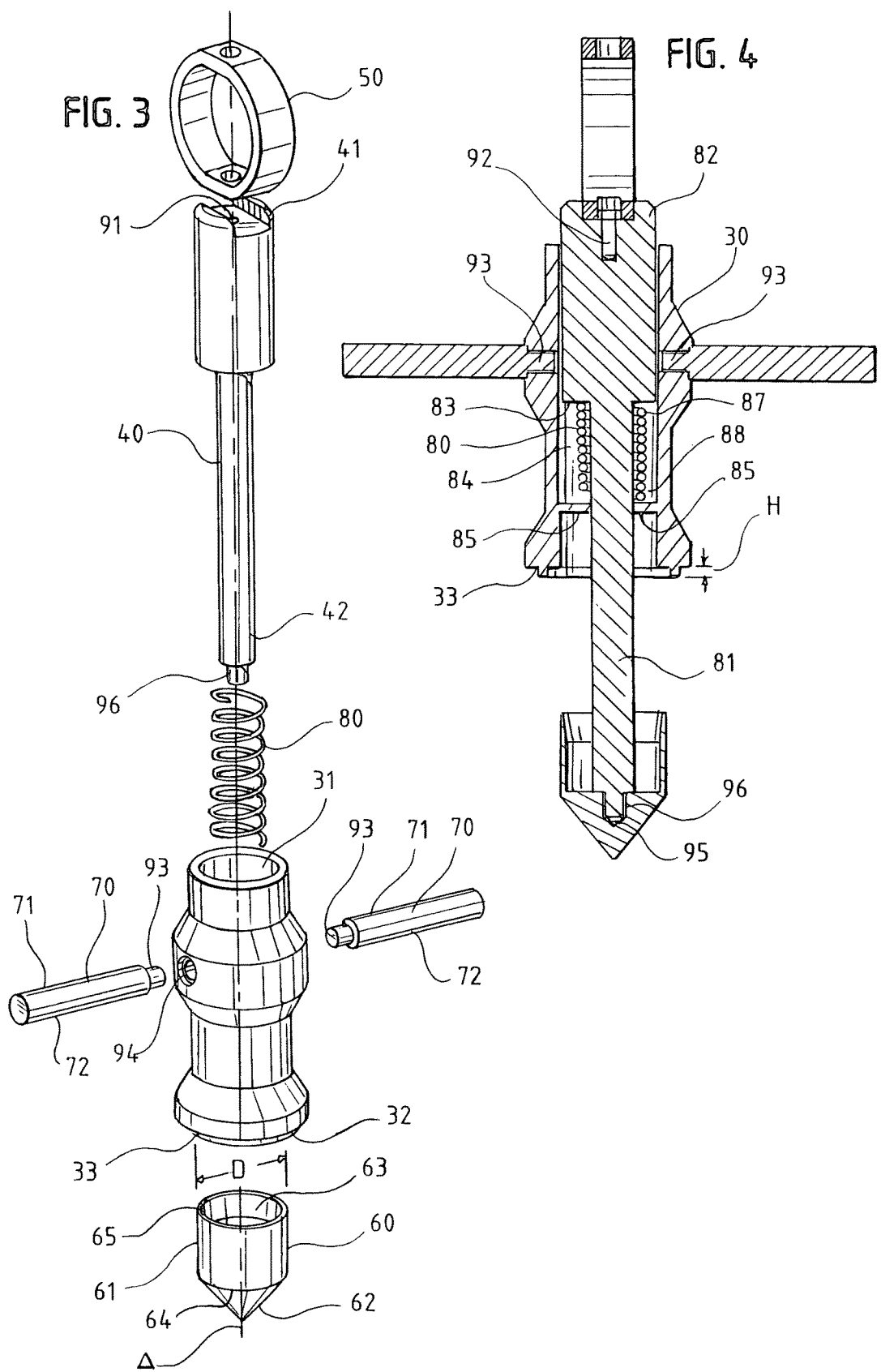

SURGICAL TOOL FOR CORING PRECISE HOLES AND PROVIDING FOR RETRIEVAL OF TISSUE

BACKGROUND

A heart pump, such as a ventricular assist device ("VAD"), aids people suffering from severe ventricular heart failure in leading active and productive lives. A heart pump is typically connected to the left ventricle of the heart. One end of a tube, such as a graft, is connected to the heart pump and the other end is connected to the ascending aorta or the descending aorta. Once connected, the heart pump pumps blood from the left ventricle to the ascending or descending aorta to improve blood flow.

To connect a heart pump to a patient, surgeons use a connector, called a sewing ring. A sewing ring attaches to the myocardium of the heart through the use of sutures. A hole is then cored in the myocardium that acts as an entry site. An inflow tube from the heart pump is inserted through this hole. For the implantation to be successful, however, the cored hole must be centered and sized appropriately so that there is minimal leaking between the ventricular wall and the inflow tube.

To initiate coring, a surgeon must first make a manual "cross" or "crux" cut in the ventricle wall. A retractable coring tool is then inserted through the crux cut and used to form the hole. If the surgeon is not careful, the hole can be formed off-center with respect to the sewing ring, or the tissue that is cored from the heart can fall into the ventricle. Either of these situations can have negative effects on the transplant procedure. For instance, if the hole is not centered relative to the sewing ring, bleeding can occur at the inflow tube—ventricle interface. Moreover, the ease of placement of the VAD is degraded. If cored tissue falls into the ventricle, the surgeon will have to retrieve the tissue, thereby increasing blood loss due to additional time added to the procedure. Accordingly, what is needed is a coring tool that allows surgeons to core a precise hole in the center of the sewing ring and to easily retrieve the cored tissue so as to prevent the tissue from falling into the ventricle.

SUMMARY OF THE INVENTION

In one embodiment, a tool for coring a hole in a patient's body is provided. The tool includes a housing with a first opening and a second opening and having an axis extending therebetween. A shaft is movably positioned along the axis. A blade assembly is attached to the shaft. An interface is attached to the housing, which is shaped and dimensioned to communicate with a connector used to connect a medical device to a person's body.

In one embodiment, the shaft comprises a first end that protrudes from the first opening and a second end that protrudes from the second opening. The first shaft end includes an actuating mechanism to allow a user to move the shaft within the housing. The actuating mechanism comprises a ring attached to the first shaft end. The blade assembly is attached to the second shaft end. The interface comprises a ridge that extends from the housing and surrounds at least a portion of the second opening of the housing. The second opening of the housing and the ridge are circular and the ridge surrounds the second opening. The blade assembly is centered with respect to the ridge. Two handle members are attached to the housing and are oriented perpendicular to the axis. The shaft rotates around the axis. The blade comprises a cup having an open end and a closed end. The open end comprises a blade edge and is circular. The closed end comprises a cone shaped protrusion. The second shaft end extends through the open end of the blade assembly and is attached to the closed end.

In one embodiment, a tool for coring a hole in a person's body is provided. The tool includes a housing with a first opening and a second opening and having an axis extending therebetween. A shaft is movably positioned along the axis. A blade assembly is attached to the shaft. The blade assembly comprises a cup having an open end and a closed end.

In one embodiment, the shaft extends through the open end and is attached to the closed end. The open end includes a blade edge. The blade edge is circular. The closed end is a cone. The shaft includes a first end protruding from the first opening and a second end protruding from the second opening. A ring is attached to the first shaft end and the blade assembly is attached to the second end. An interface is attached to the housing wherein the interface is shaped and dimensioned to communicate with a connector used to connect a medical device to a person's body.

In one embodiment, a method for coring a hole in a person's body is provided. A coring tool that includes a housing, a shaft moveably disposed within the housing, a blade assembly attached to the shaft, and an interface that is shaped and dimensioned to mate with a connector used to attach a medical device to person's body is provided. The connector is attached to the user's body. The interface is mated with the connector. The coring tool is actuated to core a hole in the person's body.

In one embodiment, the coring tool includes a blade assembly shaped like a cup having an open end and a closed end. The blade assembly is inserted into a preexisting opening in the person's body by extending the shaft such that the closed end of the blade assembly enters the person's body before the open end. The shaft is retracted after the open end enters the person's body. The shaft can also be rotated during retraction. When the shaft is retracted, the blade assembly is pulled away from the person's body.

Other objects, features and advantages of the invention will be apparent from the following detailed disclosure, taken in conjunction with the accompanying sheets of drawings, wherein like numerals refer to like parts, elements, components, steps and processes.

BRIEF DESCRIPTION OF THE DRAWINGS

FIG. 1 is a perspective view of a sewing ring attached to a portion of a heart with a crux cut shown in the spaced defined by the sewing ring.

FIG. 2A is a perspective view of a sewing ring attached to the human heart with a crux cut centered therein and a coring tool, with the blade shown retracted, prior to insertion of the cutting tool into the crux cut.

FIG. 2B is a perspective view of the coring tool of FIG. 2A with the blade shown extended after insertion of the blade assembly into the crux cut.

FIG. 2C is a perspective view of the coring tool of FIG. 2A as the blade assembly is forming a hole in the heart.

FIG. 3 is an exploded view to the coring tool of FIG. 2.

FIG. 4 is a sectional view of the coring tool of FIGS. 2A-2C taken along line 4-4 of FIG. 2B.

DETAILED DESCRIPTION

Referring to FIG. 1, a portion of a ventricle wall 1 is shown with a connector 2 for a VAD attached. In one example, the connector 2 is a sewing ring that is attached to the ventricle wall 1 through suturing. An exemplary connector can be found in the U.S. Pat. No. 9,744,279, issued on Aug. 29, 2017, for the invention entitled "Implant Connector" and naming Daniel Tamez, Vitrote Indravudh, Richard A. Marquis, Charles R. Shambaugh and Jeffrey A. LaRose as inventors, the disclosure of which is hereby incorporated by reference.

In order to connect a VAD to the ventricle wall 1, a suitable hole must be formed in the space 4 defined by sewing ring 2. Before using a coring tool, however, a surgeon must first form a "crux cut" 6 in the ventricle wall 1. The coring tool is then inserted into the crux cut 6 and actuated. The hole is then formed. The crux cut 6 is formed from a first incision 8 and a second incision 9. The first incision 8 and second incision 9 intersect to form a cross, hence the name "crux cut". In one example, a surgeon would form such a crux cut using a crux cutter. An exemplary crux cutter can be found in the United States patent application filed on the same date as the filing date of the present application, naming Rajesh Pandey as inventor and entitled "Surgical Cutting Tool for Making Precise and Accurate Incisions, U.S. patent application Ser. No. 11/332,455, filed Jan. 13, 2006, the disclosure of which is hereby incorporated by reference. The crux cut 6 is formed from a first incision 8 and a second incision 9. The first incision 8 and second incision 9 intersect to form a cross, hence the name "crux cut".

Referring to FIGS. 2A-2C, an exemplary embodiment of a coring tool 20 is shown for illustrative purposes. The coring tool 20 comprises a housing 30, a shaft 40, an actuating mechanism 50, a blade assembly 60, and handle members 70.

In one example, all of the components of the coring tool 20 are made of the same material (e.g. stainless steel). In another example, housing 30, shaft 40, actuating mechanism 50, and handle member 70 are made of one material, such as plastic, and blade assembly 60 is made of another material, such as stainless steel. Other combinations of materials are also possible depending on the needs of the end users and/or manufacturers.

Referring to FIG. 3, housing 30 includes a first opening 31 and a second opening 32. An axis A runs from first opening 31 to second opening 32. Interface 33 surrounds second opening 32. Interface 33 in one example is a circular ridge that extends out from area of the housing 30 around the second opening 32. Referring to the sectional view shown in FIG. 4, in one example, interface 33 has an outer diameter d of 0.815 inches and a height h of 0.062 inches for use with a sewing ring having the dimensions of 0.830 inches (dia) and 0.090 inches. Interface 33 is shown as being formed integrally with housing 30, but interface 33 could be a separate component that is affixed to housing 30 through other means or it could be retrofitted to an existing tool.

Shaft 40 is slidably and rotatably positioned within housing 30 and is axially and rotatably moveable with respect to axis A of housing 30. Shaft 40 includes first end 41 and a second end 42. Shaft 40 is sufficiently long that first end 41 extends out of openings 31, 32 on housing 30 when blade assembly 40 is in a retracted position (FIG. 2A) or an extended position (FIG. 2B). An exemplary length for shaft 40 is 3.70 inches given an exemplary length for housing 30 of 2.00 inches.

An actuating mechanism 50 is attached to first end 41 of shaft 40 and acts as a means to actuate coring tool 20 by pushing first end 41 toward the second opening 32 of housing 30, thereby extending blade assembly 60 from housing 30. Actuating mechanism 50 in one example is a thumb ring through which a surgeon can put a thumb. The thumb can also be used to draw shaft 40 away from the second opening 32 of housing 30 and thus move blade assembly 60 to the retracted position.

Blade mechanism 60, in one example, comprises a cup shaped member having a cylindrical portion 61 and a cone shaped portion 62. Blade mechanism 60 includes an open end 63 and a closed end 64. Open end 63 is located on one end of the cylindrical portion 61 and closed end 64 is located on one end of the cone portion 62. A blade edge 65 surrounds open end 63. Blade edge 65 in one example is circular. By applying blade edge 65 to tissue a hole can be cored in a person's heart. Advantageously, when a hole is cored in a person's heart, the cored tissue enters blade assembly 60 through open end 63. The tissue stays in blade assembly 60 until it can be retrieved by the surgeon. Cone portion 62 serves as a guide, which allows a user to pilot blade assembly 60 into a crux cut before actuating coring tool 20 to create a hole. Blade assembly 60, in one example, is formed by machining a single piece. Exemplary dimensions for blade assembly 60 are 0.90 inches overall length, with a cutting diameter of 0.620 inches and a piloting angle of 38 degrees, and a depth for the tissue retrieval section of 0.460 inches.

Handle members 70 are connected to housing 30 and are arranged perpendicular to housing 30. Handle members allow a surgeon to grasp coring tool 20 to stabilize it and apply downward pressure if necessary. The surgeon can also rest his fingers either on the top sides 71 or bottom sides 72 of handle members 70 depending on the surgeon's needs during a procedure.

In one example, blade assembly 60 is auto retractable through the provision of a resilient element, such as spring 80 disposed between housing 30 and shaft 40. Referring to FIG. 4, shaft 40 is shown as a cylinder having a first portion 81 and a second portion 82 in which the first portion 81 has a smaller diameter than the second portion 82. Exemplary diameters for the shaft 40 are 0.250 inches for the first portion 81 and 0.560 inches for the second portion 82. The difference in diameters forms a ridge 83. Similarly, housing 30 includes a first recess 84 and with protruding members 85. Spring 80 has a first end 87 that is positioned in engagement with ridge 83 and a second end 88 that is positioned in engagement with protruding members 85. Accordingly, shaft 40 and blade assembly 60 are biased by spring 80 in the retracted position.

Referring further to FIGS. 3 and 4, the various components of the core cutter 20 are connected by threads. For instance, shaft 40 has a threaded opening 91 through which a threaded protrusion 92 on ring 50 is engaged. Similarly, arm members 70 have threaded protrusions 93 that engage the threaded openings 94 on the sidewall of housing 30. Finally, the closed end 64 of blade assembly 60 has a threaded opening 95 in which a threaded protrusion 96 from shaft 40 is engaged. It should be noted that this means of attaching the components of core cutter 20 is provided for illustrative purposes only. Other means are also available depending on the materials used to form core cutter. For example, press-fitting the components together, laser welding, or gluing. The body and handles could also be formed in a single piece with injection molding, as could the shaft and ring, if those components were made of plastic or a metal capable of being injection molded.

Referring to FIGS. 2A-2C, to core a hole in a person's heart, a surgeon or other user, attaches a connecting device, such as a sewing ring 2 to a patient's ventricle 1. The surgeon will make a crux cut 6. Then, the surgeon pilots the coring tool 20 into the space 4 formed by the sewing ring 2 by communicating the interface 33 with sewing ring 2. The surgeon, if necessary, applies downward pressure on the ridge handle members 70 or simply rests his fingers on the handle members. If necessary, the surgeon inserts a thumb into ring 50. The surgeon actuates the cutting tool 10 by pressing the end 41 of the shaft 40 in the direction of the arrow shown in FIG. 2B. The blade assembly 60 enters into the ventricle until the entirety of the blade assembly 60 is in the ventricle 1. The surgeon then either (1) removes pressure from the shaft 40 and thereby allows the spring 80 to push the shaft and blade assembly up and out of the user's body or (2) applies pressure through utilization of ring 50 to propel blade assembly 60 upward in the direction of the arrow shown in FIG. 2C. In either case, the blade edge 65 engages the ventricle wall 1 and makes a hole. If need be, the surgeon can also rotate the shaft 40 around axis A to provide a rotational cutting force by the blade edge 65. The cored tissue enters opening 63 of blade assembly 60 and remains therein. The surgeon can then retrieve the cored tissue after disengaging the coring tool 20 from the sewing ring 2.

The hole formed in the ventricle wall 1 must be of a suitable size and shape to receive an inflow tube from the VAD. An exemplary hole would be one of generally circular shape and having a diameter of 15.7 mm, although the size and the shape of the hole will vary depending on the size and shape of the inflow tube on the VAD. Accordingly, for 15.7 mm diameter hole, the blade edge 65 surrounding open end 63 of blade assembly should be circular and have a diameter of 15.7 mm.

The matter set forth in the foregoing description and accompanying drawings is offered by way of illustration only and not as a limitation. While particular embodiments have been shown and described, it will be apparent to those skilled in the art that changes and modifications may be made without departing from the broader aspects of applicants' contribution. The actual scope of the protection sought is intended to be defined in the following claims when viewed in their proper perspective based on the prior art.

What is claimed is:

1. A surgical tool assembly comprising:
    a sleeve having an open end adapted for removable placement proximate to a tissue wall of a patient;
    a bladed member including a cylindrical portion defining an open end, a cone portion defining a closed end, and an opening extending therebetween, the bladed member being a cup having a cutting edge of a predetermined shape surrounding the opening, the bladed member being removably mounted on a slidable shaft for movement back and forth along a longitudinal axis of the sleeve from within the open end of the sleeve to an axially extended position outwardly from the open end of said sleeve, the cutting edge facing the open end of the sleeve when extended, the bladed member being extendable to traverse the tissue wall in one direction without any portion of the surgical tool cutting the tissue wall and retractable in the opposite direction toward the sleeve whereby the cutting edge severs a portion of the tissue wall independently of the sleeve and the bladed member retains the severed portion within the cup to form an opening in the tissue wall having said predetermined shape;
    a sewing ring configured to be attached to the tissue wall; and
    an interface comprising a ridge that extends from and surrounds a distalmost portion of a distal end of the open end of the sleeve, the ridge having a surface configured to mate with an interior surface of the sewing ring to orient the slidable shaft relative to the tissue wall and to center the ridge over the sewing ring.

2. The surgical tool assembly of claim 1, comprising in addition:
    a hollow housing portion communicating with the sleeve along said longitudinal axis of the sleeve, the slidable shaft mounted within the housing portion and having an end axially extendable from the open end of the sleeve; and
    the cup attached to the extendable shaft end, the cup having the opening therein and the closed end, the perimeter of the opening of the cup defining the cutting edge.

3. The surgical tool assembly of claim 2, having an actuating mechanism comprising a ring sized to receive at least one of a human thumb and finger attached to the slidable shaft, wherein pressure applied to the ring moves the slidable shaft.

4. The surgical tool assembly of claim 2, further comprising two handle members attached to the housing portion and being oriented perpendicular to the longitudinal axis of the sleeve, the handle members being adapted to allow a user to apply pressure on the housing portion of the surgical tool that is directed axially against the sewing ring on the tissue wall when coring a hole.

5. The surgical tool assembly of claim 2, wherein the slidable shaft is rotatable around the longitudinal axis of the sleeve such that a user can apply rotational force to the cup when cutting a hole in the tissue wall.

6. The surgical tool assembly of claim 2, wherein the cup comprises the cutting edge being substantially annular such that a substantially circular hole can be cored by utilization of the surgical tool assembly.

7. The surgical tool assembly of claim 2, wherein the cone portion is used to pilot the cup through a pre-existing cut in the tissue wall.

8. The surgical tool assembly of claim 2, wherein the slidable shaft extends into the cup and is attached within the cup at the closed end.

9. The surgical tool assembly of claim 2, in which the tissue wall comprises the muscular tissue of a heart.

10. The surgical tool assembly of claim 9, in which the sewing ring is configured to be attached to the myocardium of the heart.

11. The surgical tool assembly of claim 1, wherein the cutting edge is centered with respect to the ridge such that a user can core a hole that is centered with respect to the sewing ring.

12. The surgical tool assembly of claim 1, in which the mating surfaces of the ridge and sewing ring are annular.

13. The surgical tool assembly of claim 1, wherein the ridge extends out from the sleeve around the open end of the sleeve.

14. The surgical tool assembly of claim 1, wherein the ridge has an outer diameter of 0.815 inches and a height of 0.062 inches.

15. The surgical tool assembly of claim 1, wherein the ridge is formed integrally with the sleeve.

16. The surgical tool assembly of claim 1, wherein the ridge is separate from and affixed to the sleeve.

* * * * *